US011465794B2

(12) United States Patent
Schaffner et al.

(10) Patent No.: US 11,465,794 B2
(45) Date of Patent: Oct. 11, 2022

(54) PACKAGING LINE FOR PRE-FILLED SYRINGES AND AUTOMATED PACKAGING PROCESS

(71) Applicants: HOFFMANN-LA ROCHE INC., Little Falls, NJ (US); BAUSCH + STRÖBEL MASCHINENFABRIK ILSHOFEN GMBH+CO. KG, Ilshofen (DE)

(72) Inventors: Patrick Schaffner, Basel (CH); Marcel Felder, Basel (CH); Jürg Käser, Basel (CH); Reto Meier, Basel (CH); Jürg Mahler, Basel (CH); Wolfgang Emmert, Blaufelden (DE)

(73) Assignees: HOFFMANN-LA ROCHE INC., Little Falls, NJ (US); BAUSCH + STRÖBEL MASCHINEFABRIK ILSHOFEN GMBH + CO. KG

( * ) Notice: Subject to any disclaimer, the term of this patent is extended or adjusted under 35 U.S.C. 154(b) by 147 days.

(21) Appl. No.: 16/769,125

(22) PCT Filed: Dec. 4, 2018

(86) PCT No.: PCT/EP2018/083419
§ 371 (c)(1),
(2) Date: Jun. 2, 2020

(87) PCT Pub. No.: WO2019/110551
PCT Pub. Date: Jun. 13, 2019

(65) Prior Publication Data
US 2020/0339296 A1    Oct. 29, 2020

(30) Foreign Application Priority Data

Dec. 4, 2017  (CH) .................................. 01469/17

(51) Int. Cl.
*B65B 57/14*  (2006.01)
*A61M 5/00*  (2006.01)
(Continued)

(52) U.S. Cl.
CPC ............. *B65B 57/14* (2013.01); *A61M 5/002* (2013.01); *A61M 5/3202* (2013.01);
(Continued)

(58) Field of Classification Search
USPC ......................................................... 53/396
See application file for complete search history.

(56) References Cited

U.S. PATENT DOCUMENTS 6,164,044 A * 12/2000 Porfano ................. B65B 55/10
                                                                422/28
8,234,769 B2    8/2012  Leidig
(Continued)

FOREIGN PATENT DOCUMENTS

CN      101522240 A      9/2009
CN      103930771 A      7/2014
(Continued)

OTHER PUBLICATIONS

International Search Report dated Jan. 24, 2019 in International Application No. PCT/EP2018/083419.

*Primary Examiner* — Chinyere J Rushing-Tucker
(74) *Attorney, Agent, or Firm* — Medler Ferro Woodhouse & Mills PLLC

(57) ABSTRACT

A packaging line implemented for packaging a pre-filled syringe is disclosed having a NSD mounting station, a PFS delivery arrangement adapted to automatically deliver a pre-filled syringe to the NSD mounting station, and a NSD delivery arrangement adapted to automatically deliver a needle safety device to the NSD mounting station. The NSD mounting station is arranged to automatically assemble the
(Continued)

needle safety device to the pre-filled syringe. A NSD visual inspection station is adapted to automatically identify a pre-filled syringe with an unfit needle safety device and to automatically eliminate the identified pre-filled syringe from the packaging line. A re-insertion station is further provided to receive a pre-filled syringe with a needle safety device and to automatically feed the received pre-filled syringe, preferably from a rejected secondary packaging, back into the packaging line, after the NSD mounting station and before the NSD visual inspection station.

16 Claims, 1 Drawing Sheet

(51) Int. Cl.
    *A61M 5/32*     (2006.01)
    *B65B 65/00*     (2006.01)
    *B65C 3/02*     (2006.01)
    *B65C 9/40*     (2006.01)

(52) U.S. Cl.
    CPC .............. *B65B 65/003* (2013.01); *B65C 3/02* (2013.01); *B65C 9/40* (2013.01); *A61M 2205/60* (2013.01); *B65C 2009/402* (2013.01)

(56) References Cited

U.S. PATENT DOCUMENTS

| | | | |
|---|---|---|---|
| 9,372,180 B2 | 6/2016 | Kolb | |
| 2004/0188497 A1 | 9/2004 | Gruber et al. | |
| 2007/0017593 A1* | 1/2007 | Bernhard | B67B 3/26 |
| | | | 141/2 |
| 2008/0121537 A1* | 5/2008 | Sankaran | B65B 65/003 |
| | | | 206/223 |
| 2010/0259037 A1* | 10/2010 | Hanrahan | B65C 1/02 |
| | | | 283/81 |
| 2012/0045311 A1* | 2/2012 | Lepot | B65D 25/108 |
| | | | 414/802 |
| 2012/0241043 A1* | 9/2012 | Perazzo | A61J 7/0053 |
| | | | 141/2 |
| 2017/0275035 A1* | 9/2017 | Luciano, Jr. | B65B 1/46 |

FOREIGN PATENT DOCUMENTS

| | | |
|---|---|---|
| CN | 104554841 A | 4/2015 |
| CN | 205801576 U | 12/2016 |
| WO | 2016120185 A2 | 8/2016 |

* cited by examiner

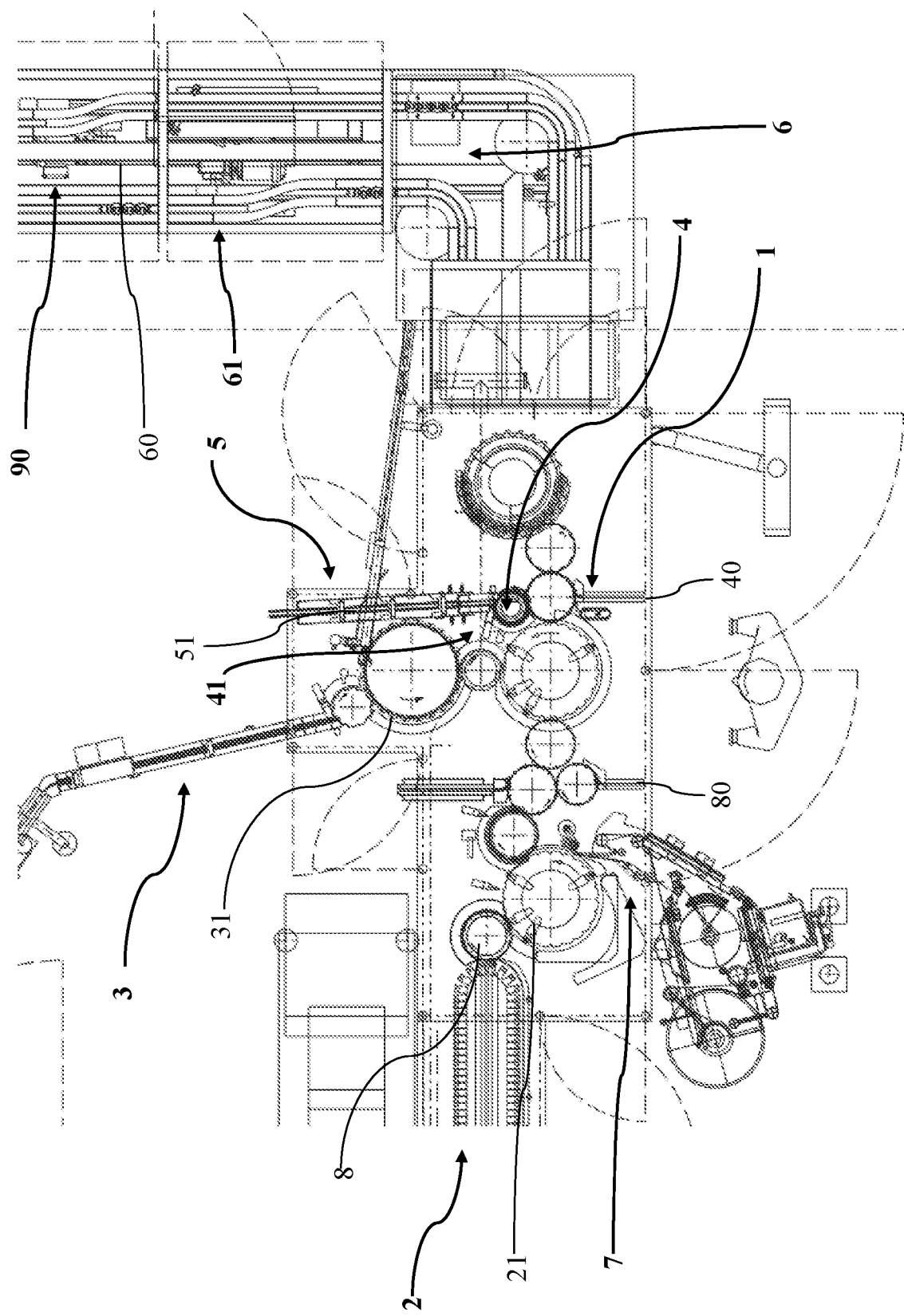

PACKAGING LINE FOR PRE-FILLED SYRINGES AND AUTOMATED PACKAGING PROCESS

TECHNICAL FIELD

The present invention relates to a packaging line for packaging a pre-filled syringe according to the preamble of independent claim 1 and, more particularly, to a packaging line adapted to automatically identify an unfit coupling of a needle safety device designed to protect a user or an operator of such pre-filled syringe from a hazardous contact with a needle component of the syringe.

Such packaging lines can be used for ensuring, by collection of information along the lines themselves, that the packaging of a pharmaceutical product, in a medical device and/or a correlated product, conforms to predetermined specifications. From this, it can result that patient safety is primarily guaranteed, that efficacy of the pharmaceutical product throughout the intended shelf life is maintained as well as that characteristics of the processed product are kept uniform and unaltered over different production lots etc. Thereby, uniformity, cleanliness, sterility, and other requirements needed to be maintained according to Good Manufacturing Practices requested by national regulatory authorities can be achieved.

The present invention also relates to an automated process of packaging a pre-filled syringe by implementation of a specially designed sequence of steps by way of and along the above mentioned packaging line.

BACKGROUND ART

A correct packaging in compliance with a validated process oftentimes reflects in the achievement of good dispensing, dosing, and ultimate usage of a pharmaceutical product. Labels, designed for instance to communicate proper use, composition data, date of batch production and/or expiration, are typically applied during packaging and also need to satisfy strict regulatory requirements.

Secondary packaging designates the packaging used to group together various products, such as pre-filled syringes, while the first layer of packaging—in direct contact with the product and normally designated primary packaging—has been already applied in previous stations of the packaging line.

Even though, conventionally, secondary packaging serves mainly branding, display for retail and logistics functions for easing transport, handling and storage of primarily package product, it is also true that secondary packaging may incorporate crucial information for the appropriate use and preservation of the products kept in the primary packaging. In the overall execution of a continuous validated packaging process—wherein a pharmaceutical product, or a device for administration of such pharmaceutical product, is delivered, packaged under given constraints and then output to be made ready for distribution—even an incorrectly executed step during secondary packaging and/or in a correlated secondary labelling can imply that a whole package such as a cardboard box, or plastic crate, containing otherwise perfectly functioning and validated pharmaceutical products, or correlated administration devices, need to be literally thrown away as unusable.

Therefore, the strict following of a predefined validate process can result in the loss of perfectly functioning medicaments and devices for the administration thereof, even as a consequence of per se trivial accidents, such as bad gluing and folding of secondary packages or issues with an accompanying leaflet.

Currently, pharmaceutical companies are forced to incinerate, or otherwise dispose of, discarded medicaments and/ or devices conceived for their administration, even if one issue emerges at the level of secondary packaging, whereas the products per se would be suitable for a normal employment.

Especially when the packaging line comprises a delicate step of coupling a needle safety device to a needle-incorporating device, such as to a pre-filled syringe, the effort linked to a correct assembly of the needle safety device and of the pre-filled syringe can be nullified downstream of the process, simply owing to a mistake or misalignment in the secondary packaging phase. Such waste of usable resources may cause considerable costs which may lower the efficiency of the overall process. This can be particularly the case if comparably expensive medicaments are involved.

Therefore, there is a need for a packaging line allowing to reduce the waste of compliant medicaments and/or devices adapted for the delivery of such medicaments, while having to dispose of such production for relatively trivial errors occurring in a secondary phase of the packaging line. There is also a need for an automated packaging process which, by operation of such a packaging line, carries out a sequence of packaging steps which allow sparing of as many products, which prove to be per se suitable for use, as possible.

DISCLOSURE OF THE INVENTION

According to the invention, this need is settled by a packaging line as it is defined by the features of independent claim 1, and by an automated packaging process as it is defined by the features of independent claim 11. Preferred embodiments are subject of the dependent claims.

In particular, the invention deals with a packaging line implemented for packaging a pre-filled syringe, comprising a NSD mounting station and a PFS delivery arrangement positioned before the NSD mounting station and adapted to automatically deliver a pre-filled syringe to the NSD mounting station.

In the context of the present invention, the term "pre-filled syringe", abbreviated by the acronym PFS, relates to a syringe, whose barrel is filled with a given dosage of pharmaceutical product. The term "pharmaceutical product" can be any substance, or medicament, or therapeutic agent, or drug to be injected, e.g. subcutaneously or intramuscularly, in a patient via the syringe. A syringe can be thought in more generic terms as a medicament delivery system, which can in principle be both manually operated—as in a conventional syringe—and automatically operated, for administering an appropriate dosage of pre-filled pharmaceutical product in the body of human or animal patients. In the present context, a syringe can also take the form of automatic injection devices, housing a container preventively filled with a pharmaceutical product, which, when operated, causes the container to move in a proximal direction towards a delivery site of the patient and a needle on the container to project out of the device housing to inject the therapeutic agent into a patient's body. This automatism is typically achieved by a mechanism, which, when triggered by an operator, automatically executes the delivery of the therapeutic agent to the patient. Therefore, the term "syringe" may also encompass injection devices intended for self-administration by patients, or for administration by untrained personnel, also known as auto-injection devices.

These devices are expressly designed to overcome manipulation and safety difficulties associated with administration of a drug through a needle-based delivery device by unskilled operators.

In connection with the invention, the term "needle safety device", abbreviated by the acronym NSD, relates to an arrangement which protects a user or operator of the syringe from the needle of the latter. An NSD typically comprises a sleeve covering the needle, after the syringe has been activated. For example, pushing a plunger rod of the syringe for administering a pre-filled medicament, or drug product, may trigger a mechanism of the NSD to move the sleeve such that it covers the needle. Typically, an NSD comprises an initially tensioned spring and a release structure interacting with the moving plunger rod. Once the plunger rod is moved for pushing the drug product out of the syringe via the needle, the release structure activates the spring which pushes the sleeve to be moved aside or around the needle.

In the present invention, a NSD delivery arrangement is positioned before the NSD mounting station and is adapted to automatically deliver a needle safety device to the NSD mounting station.

After the PFS and the NSD have reached the NSD mounting station by the respective delivery arrangements, the NSD mounting station is arranged to automatically assemble, or couple, the needle safety device to the pre-filled syringe. By a proper mounting of the needle safety device, any risk due to accidental contact with the needle by an operator after injection is prevented.

The packaging line according to the present invention comprises a NSD visual inspection station, positioned after the NSD mounting station and adapted to automatically identify a pre-filled syringe with an unfit needle safety device and to automatically eliminate the identified pre-filled syringe from the packaging line, together with the unfit needle safety device.

The term "unfit" as used in connection with the present invention can relate to an inappropriate arrangement of an element such as the needle safety device. In particular, in connection with the needle safety device this term can relate to an arrangement bearing a risk that the needle safety device is not properly triggered and/or deployed such that coverage of the needle after administration of the medicament or pharmaceutical product by the pre-filled syringe cannot be guaranteed or assured.

Also, for clarity, the terms "after" and "before" in connection with the packaging line according to the invention relate to locations with respect to a course of the packaging process. Thereby, the course of the packaging process can be defined by subsequent steps of handling the pre-filled syringes. Thus, the term "after a certain element" can be equivalent to "after the element in the course of the packaging process", or downstream of that certain element in the packaging process and the term "before a certain element" can be equivalent to "before the element in the course of the packaging process", or upstream of that certain element in the packaging process.

The packaging line is so engineered that, any time the NSD visual inspection station detects or identifies a situation wherein a needle safety device is not conformably or appropriately assembled with a pre-filled syringe, the corresponding pre-filled syringe—preferably inclusive of the defectively assembled needle safety device—is automatically eliminated, for instance via a refuse outlet diverting from the packaging line.

The term "automatically" as used in connection with some of the elements of the packaging line relates to a non-manual handling. In particular, it relates to a handling by a machine or device such that the packaging process can be executed for the most part without requiring any human interaction.

The packaging line according to the present invention advantageously comprises a re-insertion station adapted to receive a pre-filled syringe with a needle safety device and to automatically feed the received pre-filled syringe in the packaging line, after the NSD mounting station and before the NSD visual inspection station.

Whereas badly or dysfunctionally assembled pre-filled syringes and needle safety devices are discarded soon after the visual inspection section, there may in fact be, further downstream along the packaging line, some quantities of perfectly functioning and appropriately, mutually assembled pre-filled syringes and needle safety devices which may still end up being taken off the packaging line. This generally happens downstream of the packaging line at a level of a so-called secondary packaging arrangement, for reasons that lie outside a good working of the safety system incorporated by the syringes via the needle safety device.

In fact, the packaging line according to the present invention preferably comprises a secondary packaging arrangement positioned after the NSD visual inspection station and adapted to case the pre-filled syringe in a secondary packaging.

Such secondary packaging arrangement preferably comprises a packaging visual inspection station adapted to automatically identify an unfit secondary packaging and to automatically eliminate the identified packaging from the packaging line.

The secondary packaging arrangement may as well comprise a packaging labelling station, adapted to automatically equip a secondary packaging with a label. In this case, a packaging label visual inspection station may be adapted to automatically identify a packaging with an unfit label and to automatically eliminate the identified packaging from the packaging line.

The packaging line according to the invention allows for saving proper PFS, which are eliminated for reasons not directly affecting the technical functionality of the PFS and of the coupled NSD, but for non-conformities such as mislabeled or mis-formed and mis-glued secondary packages containing the PFS, or for similar flaws.

The re-insertion station of the packaging line according to the invention allows for the re-integration, back upstream into the packaging line, of such correct working PFS, which has been previously eliminated from the packaging line due to any non-conformity detected other than an inappropriate coupling with the respective NSD.

Thereby, such PFS are particularly brought back into the process, before newly undergoing a verification by the NSD visual inspection station with respect to an unfit assembly with NSD or to other non-conformities, in compliance with a continuous adherence to the validated process put in place. This allows to handle such usable PFS within the same, preferably validated, process, which ensures high quality packaged syringes.

The re-insertion of the correct working, usable PFS into the process may be, at least in part, performed manually or, preferably, automatically such as, e.g., by an appropriate robot.

Preferably, the re-insertion station comprises a feeding ramp adapted to receive the pre-filled syringe with the needle safety device and to let them slide in the packaging line. Thus, the pre-filled syringes, together with the respective correctly assembled needle safety devices, can be reintroduced in the flow of the packaging line and be submitted to a still required visual inspection at the NSD visual inspection station.

Preferably, the packaging line according to the present invention comprises a transport switch arrangement adapted to switch delivery to the NSD visual inspection station between the NSD mounting station and the re-insertion station.

Thus, it can be timely controlled that the pre-filled syringe and needle safety device assemblies submitted to the NSD visual inspection station are:

either newly created ones, resulting from the operation of the NSD mounting station, wherein the pre-filled syringes are newly sourced from the PFS delivery arrangement positioned before the NSD mounting station and the needle safety devices are newly sourced from the NSD delivery arrangement, upstream in the packaging line; or already correctly assembled ones which went past the check of the NSD visual inspection station but were taken off the packaging line downstream of the NSD visual inspection, for instance at the level of the secondary packaging arrangement.

Therefore, such transport switch arrangement allows for changing between a regular operation in which new PFS are processed; and a recycling operation in which re-inserted PFS are processed. Effective commuting between a regular flow of the packaging process, handling the pre-filled syringes newly introduced by the PFS delivery arrangement; and an alternative flow, wherein instead recycled, correctly functioning assemblies of pre-filled syringes and associated needle safety devices are fed back to the packaging line through a re-insertion station, can ensure a remarkable saving on the overall costs of manufacturing and distributing pre-filled syringes or similar medicament delivery devices. Unnecessary disposal of correctly assembled pre-filled syringes and needle safety devices can be avoided. The corresponding pre-filled pharmaceutical product, the syringes and the associated needle safety devices are accordingly spared and ready to be made available on the market.

Preferably, the NSD visual inspection station comprises a camera directed to a pre-filled syringe delivered from the NSD mounting station and a control unit adapted to automatically evaluate the images of the camera and to automatically initiate elimination of a pre-filled syringe from the packaging line if an unfit needle safety device is identified. If it is determined that the needle safety device is not properly engaged with the pre-filled syringe, then the faultily assembled syringe and associated needle safety device are taken out of the flow of the packaging line by a designated refuse outlet. This is at least the use made of the NSD visual inspection station in a situation of regular operation of the packaging line.

Preferably, the same NSD visual inspection station carries out substantially the same control function also in connection with the alternative flow of recycled pre-filled syringe and needle safety device assemblies, re-inserted through the feeding ramp and therefrom delivered to the NSD visual inspection station. Analogously, if, by any chance, it is eventually determined that any of these re-inserted component is not compliant with the specifications, then defective assemblies are taken out of the flow of the packaging line, possibly by the same refuse outlet employed for the regular operation flow.

Preferably, the packaging line according to the present invention comprises a syringe labelling station adapted to automatically equip a pre-filled syringe with a label. Such syringe labelling station may be positioned after the PFS delivery arrangement and before the NSD mounting station.

In this case, a label visual inspection station may be positioned after the syringe labelling station and be adapted to automatically identify a pre-filled syringe with an unfit label. The identified pre-filled syringe can, thus, be eliminated from the packaging line through a dedicated refuse outlet, owing to a faulty labelling.

The present invention also relates to an automated process of packaging a prefilled syringe in a packaging line, comprising the followings steps:

Automatically delivering a pre-filled syringe to a NSD mounting station. This step can be carried out by a PFS delivery arrangement of a packaging line as above described.

Automatically delivering a needle safety device to the NSD mounting station. This step can be achieved by a NSD delivery arrangement of the packaging line as above described.

Automatically assembling the needle safety device to the pre-filled syringe. This step can be implemented by the NSD mounting station.

Automatically identifying a pre-filled syringe with an unfit needle safety device. This step can be carried out by a NSD visual inspection station of the packaging line as above described.

Automatically eliminating the identified pre-filled syringe from the packaging line. This step can be initiated by a control unit adapted to evaluate the images of a camera of the NSD visual inspection device, whereby pre-filled syringes and unfit safety needle devices are recognized and consequently directed to an outlet of the packaging line, to be discarded.

The gist of the automated process of packaging a prefilled syringe according to the present invention resides in re-cycling already manufactured, rejected but nevertheless usable assemblies of pre-filled syringes and corresponding needle safety devices. This is achieved by providing a step of receiving a pre-filled syringe with a needle safety device and automatically feeding the received pre-filled syringe in the packaging line, after the NSD mounting station and before the NSD visual inspection station. Such step can be supported by a re-insertion station, which allows re-introduction in the packaging line of pre-filled syringes and associated needle safety devices, previously discarded at secondary packaging but are otherwise already correctly assembled.

Preferably, re-inserting the assembled pre-filled syringes and needle safety devices into the packaging process via the re-insertion station is automatically performed, for instance by a dedicated robot unit, but it can also be carried out, in toto or in part, manually.

Preferably, the automated process of packaging a prefilled syringe in a packaging line according to the present invention comprises the step of stopping the regular operation, that is stopping the step of automatically delivering a pre-filled syringe to the NSD mounting station, if pre-filled syringes with needle safety devices are received by the re-insertion station after the NSD mounting station. The automated process according to the present invention comprises, then, the step of feeding the pre-filled syringes received by the re-insertion station in the packaging line, before the NSD visual inspection station. These steps can be implemented by the abovementioned transport switch arrangement which allows commutation from the regular operation in which new PFS are processed to a recycling operation in which re-inserted PFS are processed.

Preferably, the pre-filled syringes with needle safety devices received by the re-insertion station are originating and are re-directed from a secondary packaging arrangement, positioned after the NSD visual inspection station.

Such secondary packaging arrangement may, for instance, be adapted to equip a secondary packaging with a label. If, by way of example through a packaging label visual inspection station, it is automatically identified that a secondary packaging has been equipped with an unfit label, the pre-filled syringes with needle safety devices therein contained are preferably re-directed from the secondary packaging arrangement and fed to the re-insertion station, so that they can be reintroduced in the packaging line.

Preferably, re-directing the above pre-filled syringes with needle safety devices comprises letting them slide back in the packaging line through a feeding ramp of the re-insertion station.

BRIEF DESCRIPTION OF THE DRAWINGS

The packaging line and the automated packaging process according to the invention are described in more detail hereinbelow by way of an exemplary embodiment and with reference to the attached FIG. 1 showing a schematic top view of a portion of a packaging line according to the present invention.

DESCRIPTION OF EMBODIMENTS

In the following description certain terms are used for reasons of convenience and are not intended to limit the invention. The terms "right", "left", "up", "down", "under" and "above" refer to directions in the FIGURES. The terminology comprises the explicitly mentioned terms as well as their derivations and terms with a similar meaning. Also, spatially relative terms, such as "beneath", "below", "lower", "above", "upper", "proximal", "distal", and the like, may be used to describe one element's or feature's relationship to another element or feature as illustrated in the FIGURES. These spatially relative terms are intended to encompass different positions and orientations of the devices in use or operation in addition to the position and orientation shown in the FIGURES. For example, if a device in the FIGURES is turned over, elements described as "below" or "beneath" other elements or features would then be "above" or "over" the other elements or features. Thus, the exemplary term "below" can encompass both positions and orientations of above and below. The devices may be otherwise oriented (rotated 90 degrees or at other orientations), and the spatially relative descriptors used herein interpreted accordingly. Likewise, descriptions of movement along and around various axes include various special device positions and orientations.

To avoid repetition in the figures and the descriptions of the various aspects and illustrative embodiments, it should be understood that many features are common to many aspects and embodiments. Omission of an aspect from a description or FIGURE does not imply that the aspect is missing from embodiments that incorporate that aspect. Instead, the aspect may have been omitted for clarity and to avoid prolix description. In this context, the following applies to the rest of this description: If, in order to clarify the drawings, a FIGURE contains reference signs which are not explained in the directly associated part of the description, then it is referred to previous or following description sections. Further, for reason of lucidity, if in a drawing not all features of a part are provided with reference signs it is referred to other drawings showing the same part. Like numbers in two or more FIGURES represent the same or similar elements.

With reference to FIG. 1, an example of a packaging line implemented for packaging a pre-filled syringe 21 according to the present invention comprises a NSD mounting station 1 and PFS delivery arrangement 2 positioned before, or upstream of, the NSD mounting station 1. The PFS delivery arrangement 2 is adapted to automatically sequentially deliver new pre-filled syringes 21 to the NSD mounting station 1 for their successive processing.

A NSD delivery arrangement 3 is also positioned before, or upstream of, the NSD mounting station 1 and is adapted to automatically deliver needle safety devices 31 to the NSD mounting station 1.

The NSD mounting station 1 is arranged to automatically assemble each of the needle safety devices 31 to a respective pre-filled syringe 21. In particular, one needle safety device 31 is upwardly clipped to one pre-filled syringe 21.

A NSD visual inspection station 4 is positioned after the NSD mounting station 1. The NSD visual inspection station 4 is adapted to automatically identify a non-compliant mounting of pre-filled syringe 21 with an unfit needle safety device 31 and to automatically eliminate the identified pre-filled syringe 21, together with the unfit needle safety device 31, from the packaging line.

To this purpose, the NSD visual inspection station 4 comprises a camera directed to one of the pre-filled syringes 21 delivered from the NSD mounting station 1 and a control unit adapted to automatically evaluate the images of the camera and to automatically initiate elimination of a pre-filled syringe 21 from the packaging line if an unfit needle safety device 31 is identified. More specifically, if it is detected that a pre-filled syringe 21 does not come to engage a respective needle safety device in a pre-defined fashion from the NSD mounting station 1, the non-compliant assembly of such syringe 21 with the respective needle safety device 31 is removed from the packaging line via a refuse outlet 40.

A re-insertion station 5 is adapted to receive a pre-filled syringe 21 with a needle safety device 31 and to automatically feed the received pre-filled syringe 21, together with the mounted-on needle safety device 31, in the packaging line, after the NSD mounting station 1 and before the NSD visual inspection station 4.

The re-insertion station 5 allows for the advantageous and economical re-integration, back into the packaging line, of usable PFS, which are eliminated from the packaging line due to any non-conformity detected and which may not be technically affecting the proper functioning of the safety system created by mounting the needle safety devices 31 on the pre-filled syringes 21. Thereby, such pre-filled syringes are particularly brought back into the process, before being—once more—verified in relation to an unfit NSD or to any other non-conformity at the NSD visual inspection station 4. This allows to handle such re-integrated PFS within the same, preferably validated, process, thereby still ensuring the high quality of the packaged syringes. A transport switch arrangement 41 is provided, which transport switch arrangement is configured to switch delivery to the NSD visual inspection station 4 between the NSD mounting station 1 and the re-insertion station 5. In an exemplary embodiment, the transport switch arrangement 41 comprises a switching member which, in a first position, connects the feeding ramp 51 of the re-insertion station 5 to the NSD visual inspection station 4 and disconnects the NSD mounting station 1 from the NSD visual inspection station 4. Vice versa, in a second position, the switching member disconnects the feeding ramp 51 of the re-insertion station 5 from the NSD visual inspection station 4 and connects the NSD mounting station 1 to the NSD visual inspection station 4.

In the embodiment shown in FIG. 1, the packaging line according to the invention allows for saving properly functioning PFS, which have been previously eliminated for reasons linked to mis-labelling or erroneous box packing of secondary packages and the like, further downstream in the packaging process.

In fact, a secondary packaging arrangement 6 is positioned after the NSD visual inspection station 4 and adapted to case the pre-filled syringes 21, together with the mounted needle safety devices 31, in a secondary packaging.

As already mentioned, the secondary packaging arrangement 6 comprises a packaging visual inspection station 61 adapted to automatically identify an unfit secondary packaging and to automatically eliminate the identified packaging from the packaging line. A secondary packaging which is wrongly box packed is therefore detected by the above packaging visual inspection station 61 as unfit.

Further, the secondary packaging arrangement 6 comprises a packaging labelling station 60 adapted to automatically equip a secondary packaging with a label. In this respect, to guarantee compliance, a packaging label visual inspection station 90 is provided which is adapted to automatically identify a packaging with an unfit label and to automatically eliminate the identified packaging from the packaging line.

The re-insertion station 5 comprises a feeding ramp 51 adapted to receive the pre-filled syringes 21, together with their respective needle safety devices 31, which are to be re-integrated into the packaging line. Through the ramp 51, the assemblies of pre-filled syringes 21 and needle safety devices 31 are let slide back into the packaging line, ready to be examined again by the NSD visual inspection station 4.

The pre-filled syringes 21 newly introduced in the packaging line via the PFS delivery arrangement 2, are automatically equipped with labels at a syringe labelling station 7.

A label visual inspection station 8, positioned after the syringe labelling station 7, is adapted to automatically identify a pre-filled syringe 21 with an unfit label and to automatically eliminate the identified pre-filled syringe 21 from the packaging line. Thus, an improperly labelled pre-filled syringe 21 can be disposed of before reaching the NSD mounting station 1, through a refuse outlet 80.

This description and the accompanying drawings that illustrate aspects and embodiments of the present invention should not be taken as limiting the claims defining the protected invention. In other words, while the invention has been illustrated and described in detail in the drawings and foregoing description, such illustration and description are to be considered illustrative or exemplary and not restrictive. Various mechanical, compositional, structural, electrical, and operational changes may be made without departing from the spirit and scope of this description and the claims. In some instances, well-known circuits, structures and techniques have not been shown in detail in order not to obscure the invention. Thus, it will be understood that changes and modifications may be made by those of ordinary skill within the scope and spirit of the following claims. In particular, the present invention covers further embodiments with any combination of features from different embodiments described above and below.

The disclosure also covers all further features shown in the FIGS. individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims or the exemplary embodiments as well as subject matter comprising said features.

Furthermore, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Components described as coupled or connected may be electrically or mechanically directly coupled, or they may be indirectly coupled via one or more intermediate components. Any reference signs in the claims should not be construed as limiting the scope.

The invention claimed is:

1. A packaging line implemented for packaging a pre-filled syringe, comprising:
    a needle safety device (NSD) mounting station;
    a pre-filled syringe (PFS) delivery arrangement positioned before the NSD mounting station and configured to automatically deliver a pre-filled syringe to the NSD mounting station;
    a needle safety device (NSD) delivery arrangement positioned before the NSD mounting station and configured to automatically deliver a needle safety device to the NSD mounting station;
    a needle safety device (NSD) visual inspection station; and
    a re-insertion station,
    wherein the NSD mounting station is arranged to automatically assemble the needle safety device to the pre-filled syringe,
    wherein the NSD visual inspection station is positioned after the NSD mounting station and configured to automatically identify a pre-filled syringe with an unfit needle safety device and to automatically eliminate the identified pre-filled syringe from the packaging line, and
    wherein the re-insertion station is configured to receive a pre-filled syringe with a needle safety device and to automatically feed the received pre-filled syringe into the packaging line after the NSD mounting station and before the NSD visual inspection station.

2. The packaging line of claim 1, comprising a transport switch arrangement configured to switch delivery to the NSD visual inspection station between the NSD mounting station and the re-insertion station.

3. The packaging line of claim 1, comprising a syringe labelling station configured to automatically equip a pre-filled syringe with a label.

4. The packaging line of claim 3, comprising a label visual inspection station positioned after the syringe labelling station and configured to automatically identify a pre-filled syringe with an unfit label and to automatically eliminate the identified pre-filled syringe from the packaging line.

5. The packaging line of claim 1, comprising a secondary packaging arrangement positioned after the NSD visual inspection station and configured to case the pre-filled syringe in a secondary packaging.

6. The packaging line of claim 5, wherein the secondary packaging arrangement comprises a packaging visual inspection station configured to automatically identify an unfit secondary packaging and to automatically eliminate the identified secondary packaging from the packaging line.

7. The packaging line of claim 5, wherein the secondary packaging arrangement comprises a packaging labelling station configured to automatically equip the secondary packaging with a label.

8. The packaging line of claim 7, comprising a packaging label visual inspection station configured to automatically identify a secondary packaging with an unfit label and to automatically eliminate the identified secondary packaging from the packaging line.

9. The packaging line of claim 1, wherein the re-insertion station comprises a feeding ramp configured to receive the pre-filled syringe with the needle safety device and to let slide the pre-filled syringe in the packaging line.

10. The packaging line of claim 1, wherein the NSD visual inspection station comprises a camera directed to a pre-filled syringe delivered from the NSD mounting station and a control unit configured to automatically evaluate the images of the camera and to automatically initiate elimination of a pre-filled syringe from the packaging line if an unfit needle safety device is identified.

11. An automated process of packaging a prefilled syringe, comprising the steps of:
automatically delivering a pre-filled syringe to a needle safety device (NSD) mounting station;
automatically delivering a needle safety device to the NSD mounting station;
automatically assembling the needle safety device to the pre-filled syringe;
automatically identifying a pre-filled syringe with an unfit needle safety device;
automatically eliminating the identified pre-filled syringe from the packaging line; and
receiving pre-filled syringes with needle safety devices and automatically feeding the received pre-filled syringes in the packaging line, after the NSD mounting station and before a needle safety device (NSD) visual inspection station.

12. The automated process of claim 11, comprising the steps of:
stopping automatically delivering a pre-filled syringe to the NSD mounting station, if pre-filled syringes with needle safety devices are received by the re-insertion station, and
feeding the pre-filled syringes received by the re-insertion station in the packaging line, before the NSD visual inspection station.

13. The automated process of claim 11, comprising the step of redirecting the pre-filled syringes with needle safety devices received by the re-insertion station from a secondary packaging arrangement positioned after the NSD visual inspection station.

14. The automated process of claim 13, comprising the step of letting the pre-filled syringes with needle safety devices slide in the packaging line through a feeding ramp of the re-insertion station.

15. The automated process of claim 13, comprising the step of equipping a secondary packaging with a label, by the secondary packaging arrangement, and automatically identifying a secondary packaging with an unfit label, by a packaging label visual inspection station.

16. The automated process of claim 15, wherein the pre-filled syringes with needle safety devices contained in a secondary packaging with an unfit label are redirected to the re-insertion station.

* * * * *